(12) United States Patent
Cho et al.

(10) Patent No.: US 7,371,897 B1
(45) Date of Patent: May 13, 2008

(54) PREPARATION METHOD FOR (Z)-7-CHLORO-((S)-2,2-DIMETHYLCYCLO-PROPANECARBOXAMIDO)-2-HEPTENOIC ACID

(75) Inventors: Yang Rai Cho, Ulsan (KR); Young Ji Shim, Ulsan (KR); Eon Cheol Koo, Ulsan (KR); Seon Yi Jeong, Ulsan (KR); Byung Hwan Kim, Ulsan (KR)

(73) Assignee: Wischem Co., Ltd., Ulsan (KR)

( * ) Notice: Subject to any disclaimer, the term of this patent is extended or adjusted under 35 U.S.C. 154(b) by 0 days.

(21) Appl. No.: 11/784,790

(22) Filed: Apr. 10, 2007

(30) Foreign Application Priority Data

Dec. 11, 2006  (KR) .................... 10-2006-0125284

(51) Int. Cl.
*C07C 205/00* (2006.01)
*C07C 229/00* (2006.01)
(52) U.S. Cl. ...................... 562/553; 562/567
(58) Field of Classification Search ............ None
See application file for complete search history.

(56) References Cited

U.S. PATENT DOCUMENTS 5,147,868 A * 9/1992 Graham et al. ............ 514/119
2005/0119346 A1* 6/2005 Kumar et al. .............. 514/562

FOREIGN PATENT DOCUMENTS

WO    WO2006022511    * 3/2006

OTHER PUBLICATIONS

Graham et al. Inhibition of the Mammalian B-Lactamae Renal Dipeptidase (Dehydropeptidase-I) by (Z)-2-(Acylamino)-3-substituted- propenoic Acids. Journal of Medicinal Chemistry, 1987, vol. 30, pp. 1074-1090.*

* cited by examiner

*Primary Examiner*—Sikarl A. Witherspoon
(74) *Attorney, Agent, or Firm*—Henry D. Coleman; R. Neil Sudol; William J. Sapone

(57) ABSTRACT

Provided is a novel preparation method of (Z)-7-chloro-((S)-2,2-dimethylcyclopropanecarboxamido)-2-heptenoic acid represented by the following formula (1), a key intermediate of cilastatin used as a supplement to imipenem. The novel preparation method of the invention produces a pure (Z)-7-chloro-((S)-2,2-dimethylcyclopropanecarboxamido)-2-heptenoic acid, a key intermediate of cilastatin, by selective hydrolysis of E isomers.

5 Claims, No Drawings

PREPARATION METHOD FOR (Z)-7-CHLORO-((S)-2,2-DIMETHYLCYCLO-PROPANECARBOXAMIDO)-2-HEPTENOIC ACID

CROSS-REFERENCE TO RELATED APPLICATION

This application is based on and claims priority from Korean Patent Application No. 10-2006-125284, filed on Dec. 11, 2006 in the Korean Intellectual Property Office, the disclosure of which is incorporated herein in its entirety by reference.

BACKGROUND OF THE INVENTION

1. Field of the Invention

The present invention relates to a novel preparation method of (Z)-7-chloro-((S)-2,2-dimethylcyclopropanecarboxamido)-2-heptenoic acid represented by the following formula (1), a key intermediate of cilastatin used as a supplement to imipenem.

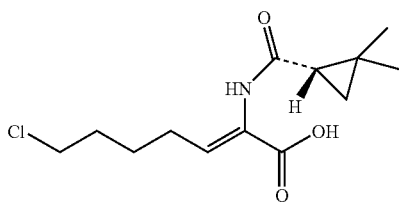

2. Description of the Prior Art

Conventional processes for the preparation of (Z)-7-chloro-((S)-2,2-dimethylcyclopropanecarboxamido)-2-heptenoic acid represented by the following formula (1) or its inorganic salt are described or mentioned in European Patent No. 48301, WO 2006/022511, and US Patent Application No. 2005/0119346.

According to the description in WO 2006/022511, ethyl (Z)-7-chloro-((S)-2,2-dimethylcyclopropanecarboxamido)-2-heptenoate was mixed with (E)-7-chloro-((S)-2,2-dimethylcyclopropanecarboxamido)-2-heptenoic acid ester (3), as shown in the following <Reaction Formula I>, at a ratio of about 85-90%: about 10-13% to prepare an isomer. The isomer mixture was then partially hydrolyzed with an alkali added at an amount less than equivalence to the titration, and a (Z)-7-chloro-((S)-2,2-dimethylcyclopropanecarboxamido)-2-heptenoic acid alkali metal salt (aq) was extracted. The extracted salt was concentrated and purified by crystallization from an organic solvent.

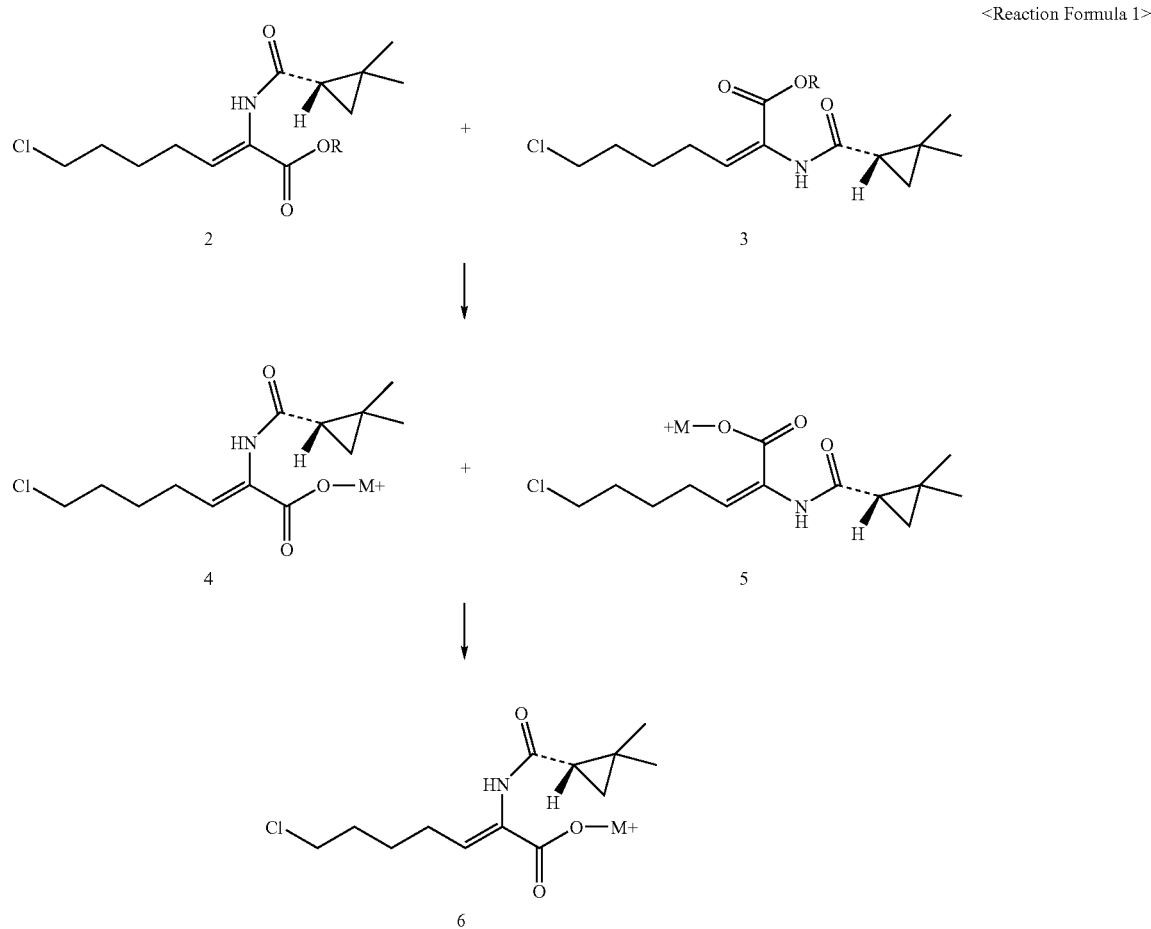

<Reaction Formula 1>

However, this method is low in alkali-hydrolysis selectivity. Therefore, even though the hydrolysis was done with addition of an alkali at an amount less than equivalence to the titration, a considerable amount of (E) isomer and (Z) isomers are hydrolyzed together and an aqueous solution of an alkali salt being recovered, i.e., an aqueous solution of (Z)-7-chloro-((S)-2,2-dimethylcyclopropanecarboxamido)-2-heptenoic acid alkali metal salt, contains a substantial amount of the (E) isomers. To purify the solution, most of water was concentrated and removed, and a suitable organic solvent was added for crystallization. Unfortunately, purity of the resultant (Z)-7-chloro-((S)-2,2-dimethylcyclopropanecarboxamido)-2-heptenoic acid alkali metal salt is very low, despite these strict conditions.

According to U.S. Pat. No. 5,147,868, in order to remove (E)-isomers, a (Z)-7-chloro-((S)-2,2-dimethylcyclopropanecarboxamido)-2-heptenoic acid mixture containing a large amount of E isomers was used to prepare a cilastatin intermediate. This cilastatin intermediate was heated under acidic conditions for purification.

However, this method is disadvantageous in that hydrolysis following the heating operation under acidic conditions not only produced unknown impurities but also a respectable amount of the mixture was decomposed to (S)-2,2-dimethylcyclopropanecarboxamido which is very difficult to remove in practice. This is also mentioned in WO 2006/022511.

Therefore, there is a need to develop a new method for the preparation of (Z)-7-chloro-((S)-2,2-dimethylcyclopropanecarboxamido)-2-heptenoic acid of high purity in need of the efficient synthesis of cilastatin.

SUMMARY OF THE INVENTION

Accordingly, the present invention has been made to solve the above-mentioned problems occurring in the prior art, and an object of the present invention is to provide a novel preparation method of (Z)-7-chloro-((S)-2,2-dimethylcyclopropanecarboxamido)-2-heptenoic acid, a key intermediate of cilastatin used as a supplement to imipenem.

It is another object of the present invention to provide a novel, efficient preparation method of (Z)-7-chloro-((S)-2,2-dimethylcyclopropanecarboxamido)-2-heptenoic acid with purity greater than 99%.

In order to achieve the above objects, there is provided a preparation method for 7-chloro-((S)-2,2-dimethylcyclopropanecarboxamido)-2-heptenoic acid, including the steps of:

(a) mixing ethyl(Z)-7-chloro-((S)-2,2-dimethylcyclopropanecarboxamido)-2-heptenoate represented by the following formula (2) and ethyl (E)-7-chloro-((S)-2,2-dimethylcyclopropanecarboxamido)-2-heptenoate represented by the following formula (3), and selectively hydrolyzing the ethyl (E)-7-chloro-((S)-2,2-dimethylcyclopropanecarboxamido)-2-heptenoate with an acid;

(b) neutralizing the resultant acid solution of the step (a) with an alkali, and alkali-hydrolyzing the ethyl (Z)-7-chloro-((S)-2,2-dimethylcyclopropanecarboxamido)-2-heptenoate to prepare an alkali aqueous solution of (Z)-7-chloro-((S)-2,2-dimethylcyclopropanecarboxamido)-2-heptenoic acid, and isolating a supernatant liquid; and (c) neutralizing the isolated supernatant (aqueous phase) from the step (b) and extracting with an organic solvent, and performing a purification procedure that involves drying, concentrating, filtering and separating the organic phase, to obtain (Z)-7-chloro-((S)-2,2-dimethylcyclopropanecarboxamido)-2-heptenoic acid represented by the following formula (1),

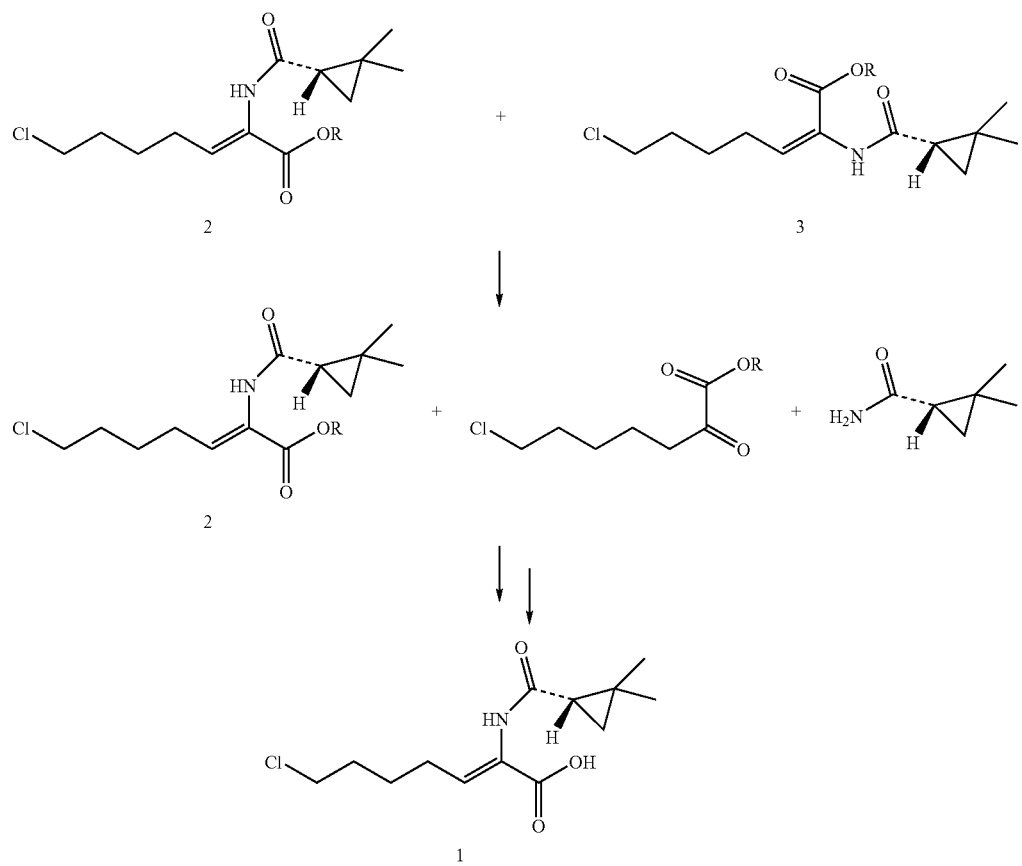

DETAILED DESCRIPTION OF THE PREFERRED EMBODIMENTS

Hereinafter, preferred examples of the present invention will be described. The matters defined in the description are nothing but specific details provided to assist those of ordinary skill in the art in a comprehensive understanding of the invention, and thus the present invention is not limited thereto.

The ethyl (Z)-7-chloro-((S)-2,2-dimethylcyclopropanecarboxamido)-2-heptenoate represented by the formulas (2) is mixed with an (E)-isomer represented by the formulas (3) according to the process disclosed in European Patent No. 48301. To selectively hydrolyze the (E)-isomer from the mixture in the step (a), a solvent that has good reactivity and workability is used. Examples of such solvent preferably include, but are not limited to, alcohols, ethers, nitrils, sulfoxides, ketones, amides, carbon chlorides, aromatic organic solvents, and mixtures thereof. In particular, tetrahydrofuran, 1,4-dioxane, acetonitrile, benzene, toluene, dichloromethane, dichloroethane, or a mixture of these is used.

Examples of an acid used for selective hydrolysis of ethyl (E)-7-chloro-((S)-2,2-dimethylcyclopropanecarboxamido)-2-heptenoate represented by the formulas (3) in the step (a) preferably include, but are not limited to, organic acids such as hydrochloric acid, bromic acid, sulfuric acid, and phosphoric acid; inorganic acids such as acetic acid, formic acid, trifluoroacetic acid, and trichloroacetic acid; and sulfonic acids such as methyl sulfonic acid, benzene sulfonic acid, and toluene sulfonic acid, in which the acid is 0.05 equivalent, preferably 0.5-1.5 equivalent, with respect to the esters.

In the step (a), the reaction occurs at a temperature in the range of 0 to 100° C., preferably, 20-40° C. The reaction ends at the point where a mol ratio of the (Z)-isomer represented by the formula (2) to the (E)-isomer represented by the formula (3) according to gas chromatograph assay, is 100:1 or greater, preferably 150:1 or greater, and more preferably 200:1 or greater.

Examples of the alkali used in the step (b) preferably include, but are not limited to, NaOH, $Na_2CO_3$, KOH, $K_2CO_3$, and LiOH, in which the akali is 1 equivalent, preferably 1-2 equivalent, with respect to the ester. The reaction occurred at a temperature in the range of 0-100° C., preferably 20-40° C.

Examples of the acid used for neutralization in the step (C) preferably include, but are not limited to, inorganic acids such as hydrochloric acid, bromic acid, sulfuric acid, nitric acid, and phosphoric acid; or organic acids such as acetic acid and formic acid.

Examples of the organic solvent for extraction in the step (C) preferably include, but are not limited to, esters such as ethyl acetate and butyl acetate, ethers such as diethyl ether, isopropyl ether and butyl ether, aromatic organic solvents such as benzene and toluene, carbon chlorides such as dichloromethane and dichloroethane, and mixtures of these or organic solvents that can be mixed with the organic solvents.

Hereinafter, the invention is explained in more detail with reference to the following examples. However, the following examples are for illustrative purposes only, and are not to limit the invention.

Ref. Ex. 1

Preparation of Ethyl (Z)-7-chloro-((S)-2,2-dimethyl-cyclopropanecarboxamido)-2-heptenoate (2)

As described in European Patent No. 48301, 250 g of ethyl 7-chloro-2-oxoheptanoate and 141 g of (S)-2,2-dimethyl cyclopropanecarboxamid were reacted and concentrated. In result, 372.4 g of ethyl (Z)-7-chloro-((S)-2,2-dimethylcyclopropanecarboxamido)-2-hepnoate (2) containing, by gas chromatography assay, 10.5% of ethyl (E)-7-chloro-((S)-2,2-dimethylcyclopropanecarboxamido)-2-heptenoate (3) was obtained.

Ex. 1

Preparation of (Z)-7-chloro-((S)-2,2-dimethylcyclo-propanecarboxamido)-2-heptenoic acid (1)

200 g (0.66 mol) of ethyl (Z)-7-chloro-((S)-2,2-dimethylcyclopropanecarboxamido)-2-heptenoate (2) obtained from the Ref. Ex. 1 was dissolved in 600 ml of dichloromethane. 126 g of 4-toluenesulfonic acid was added to the mixture and stirred at 20° C. When a (mol) ratio of the ethyl (Z)-7-chloro-((S)-2,2-dimethylcyclopropanecarboxamido)-2-heptenoate (2) to the ethyl (E)-7-chloro-((S)-2,2-dimethylcyclopropanecarboxamido)-2-heptenoate (3) was about 200:1 according to gas chromatography assay, the pH of the mixture was adjusted to 8-9 by adding 0.5N caustic soda solution, and an organic phase was isolated. The isolated organic phase was concentrated under reduced pressure and provided to 1,000 ml of acetonitrile. Next, 1,420 ml (0.925 mole) of 0.65N caustic soda solution was added and stirred at room temperature until ethyl (Z)-7-chloro-((S)-2,2-dimethylcyclopropanecarboxamido)-2-heptenoate (2) was completely reacted. Most of acetonitrile was evaporated under reduced pressure, and an aqueous phase was washed with 270 ml of dichloromethane. The pH of the aqueous phase was adjusted to 3.5 by adding hydrochloric acid and extracted from 670 ml of dichloromethane. Meanwhile, the organic phase was provided into 70 g of anhydrous magnesium sulfate, stirred, filtered and concentrated under reduced pressure. The residual was crystallized from a mixed solvent of ethyl acetate and n-hexane (about 1:4), filtered and dried in hot air at 40° C. for 10 hours to produce 101.4 g of the target compound, (Z)-7-chloro-((S)-2,2-dimethylcyclopropanecarboxamido)-2-heptenoic acid (1).

HPLC(C18, 40% aqueous acetonitrile solution) purity: 99.1%, (Z)/(E)=910

H1 nmr ($CDCl_3$, 500 MHz) ppm: 0.82-0.84 (dd, 1H), 1.15-1.23 (s, 7H), 1.43-1.46 (dd, 1H), 1.61-1.67 (m, 2H), 1.78-1.83 (m, 2H), 2.19-2.23 (m, 2H), 3.53-3.56 (t, 2H), 6.77-6.79 (t, 1H), 6.99 (s, 1H)

Ex. 2

Preparation of (Z)-7-chloro-((S)-2,2-dimethylcyclo-propanecarboxamido)-2-heptenoic acid (1)

100 g (0.33 mol) of ethyl (Z)-7-chloro-((S)-2,2-dimethylcyclopropanecarboxamido)-2-heptenoate (2) obtained from the Ref. Ex. 1 was dissolved in 300 ml of toluene. 47 g of methyl sulfonic acid was added to the mixture and stirred at 30° C. When a (mol) ratio of the ethyl (Z)-7-chloro-((S)-2,2-dimethylcyclopropanecarboxamido)-2-heptenoate (2) to the ethyl (E)-7-chloro-((S)-2,2-dimethylcyclopropanecarboxamido)-2-heptenoate (3) was about 120:1 according to gas chromatography assay, the reaction was ended, and the mixture was stirred. The pH of the mixture was adjusted to 8-9 by adding 0.5N caustic soda solution, and an organic phase was isolated. The isolated organic phase was concentrated under reduced pressure and provided to 300 ml of ethanol. Next, 380 ml (0.46 mole) of 1.2N caustic soda solution was added and stirred at room temperature until ethyl (Z)-7-chloro-((S)-2,2-dimethylcyclopropanecarboxamido)-2-heptenoate (2) was completely reacted. Most of ethanol was evaporated under reduced pressure, and an aqueous phase was washed with 150 ml of dichloromethane. The pH of the aqueous phase was adjusted to 3.5 by adding 35% hydrochloric acid and extracted from 1,500 ml of isoprophyl ether. Meanwhile, the organic phase was provided into 100 g of anhydrous magnesium sulfate, stirred, filtered and concentrated under reduced pressure. The filtrate was crystallized, filtered and dried in hot air at 40° C. for 10 hours to produce 50.5 g of the target compound, (Z)-7-chloro-((S)-2,2-dimethylcyclopropanecarboxamido)-2-heptenoic acid (1).

HPLC(C18, 40% aqueous acetonitrile solution) purity: 99.3%, (Z)/(E)=540

H1 nmr (CDCl$_3$, 500 MHz) ppm: 0.82-0.84 (dd, 1H), 1.15-1.23 (s, 7H), 1.43-1.46 (dd, 1H), 1.61-1.67 (m, 2H), 1.78-1.83 (m, 2H), 2.19-2.23 (m, 2H), 3.53-3.56 (t, 2H), 6.77-6.79 (t, 1H), 6.99 (s, 1H)

Ex. 3

Preparation of Aqueous Cilastatin Solution 34.4 g of (Z)-7-chloro-((S)-2,2-dimethylcyclopropanecarboxamido)-2-heptenoic acid (1) obtained from Ex. 1 was dissolved in mixed aqueous solution of L-cystein hydrochloric acid salt (20 g) and caustic soda solution (116 ml) and stirred at room temperature. The reaction was continued until (Z)-7-chloro-((S)-2,2-dimethylcyclopropanecarboxamido)-2-heptenoate (2) was fully consumed according to high speed liquid chromatograph assay. In result, high purity aqueous cilastatin solution showing only a faint trace of E isomers was obtained.

In preparation of cilastatin, a key antibiotics supplement such as imipenem, the method of removing isomer impurities is very important. In this light, the present invention method is industrially useful in that a simple selective acid-hydrolysis removes a substantial amount of E-isomer impurities in the preparation process of (Z)-7-chloro-((S)-2,2-dimethylcyclopropanecarboxamido)-2-heptenoic acid, which is an essential intermediate for preparing cilastatin, and high purity cilastatin can easily prepared.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A preparation method for (Z)-7-chloro-((S)-2,2-dimethylcyclopropanecarboxamido)-2-heptenoic acid, comprising the steps of:
    a) Acid-hydrolyzing the ethyl (E)-7-chloro-((S)-2,2-dimethylcyclopropanecarboxamido)-2-heptenoate selectively in the mixture of ethyl (Z)-7-chloro-((S)-2,2-dimethylcyclopropane carboxamido)-2-heptenoate and ethyl (E)-7-chloro-((S)-2,2-dimethylcyclopropanecarboxamido)-2-heptenoate;
    b) alkali-hydrolyzing obtained ethyl (Z)-7-chloro-((S)-2,2-dimethylcyclopropanecarboxamido)-2-heptenoate in step a) to obtain pure (Z)-7-chloro-((S)-2,2-dimethylcyclopropanecarboxamido)-2-heptenoic acid.

2. The method of claim 1, wherein the pure (Z)-7-chloro-((S)-2,2-dimethylcyclopropanecarboxamido)-2-heptenoic acid contains Z isomers and E isomers at mol ratio of 200:1 or greater.

3. The method of claim 1, wherein the solvent used for acid hydrolysis is selected from a group consisting of ethers, nitrils, sulfoxides, ketones, amides, carbon chlorides, alcohols, aromatic organic solvents, and mixtures thereof.

4. The method of claim 3, wherein the solvent used for acid hydrolysis is selected from a group consisting of tetrahydrofuran, 1,4-dioxane, acetonitrile, benzene, toluene, dichloromethane, dichloroethane, or a mixture thereof.

5. The method of claim 1, wherein the acid used for acid hydrolysis is selected from a group consisting of hydrochloric acid, bromic acid, sulfuric acid, phosphoric acid, acetic acid, formic acid, trifluoroacetic acid, trichloroacetic acid, methyl sulfonic acid, benzenesulfonic acid, toluenesulfonic acid, and trifluoroboran.

* * * * *